United States Patent
Popovic et al.

(10) Patent No.: US 11,980,505 B2
(45) Date of Patent: May 14, 2024

(54) VISUALIZATION OF DEPTH AND POSITION OF BLOOD VESSELS AND ROBOT GUIDED VISUALIZATION OF BLOOD VESSEL CROSS SECTION

(71) Applicant: KONINKLIJKE PHILIPS N.V., Eindhoven (NL)

(72) Inventors: Aleksandra Popovic, Boston, MA (US); Haytham Elhawary, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/984,683

(22) Filed: Nov. 10, 2022

(65) Prior Publication Data

US 2023/0065264 A1    Mar. 2, 2023

Related U.S. Application Data

(63) Continuation of application No. 15/115,846, filed as application No. PCT/IB2015/050551 on Jan. 26, 2015, now Pat. No. 11,523,874.

(Continued)

(51) Int. Cl.
*A61B 90/00* (2016.01)
*A61B 1/00* (2006.01)
(Continued)

(52) U.S. Cl.
CPC .......... *A61B 90/37* (2016.02); *A61B 1/00009* (2013.01); *A61B 1/000094* (2022.02);
(Continued)

(58) Field of Classification Search
CPC . G06T 2207/30101; G06T 2207/30048; A61B 34/10; A61B 1/000094; A61B 1/0005; A61B 34/30; A61B 34/20
See application file for complete search history.

(56) References Cited

U.S. PATENT DOCUMENTS

2004/0082850 A1   4/2004   Bonner et al.
2004/0138685 A1   7/2004   Clague et al.
(Continued)

FOREIGN PATENT DOCUMENTS

JP   2012235983 A   12/2012
WO   2008095068      8/2008
(Continued)

OTHER PUBLICATIONS

Mori, K. et al "Tracking of a Bronchoscope using Epipolar Geometry Analysis and Intensity-Based Image Regisration of Real and Virtual Endoscopic Images", Medical Image Analysis, vol. 6, 2002, pp. 321-336.
Linte, Cristian A. et al "Augmented Environments for Computer-Assisted Interventions, 6th International Workshop, AE-CA1 2011;" 2D/3D Registration of a Preoperative Model with Encoscopic Video using Colour-Consistency, LNCS 7264, pp. 1-12, 2012.
From Wikipedia "X-Ray Computed Tomography", 2014.
(Continued)

*Primary Examiner* — Alexandra L Newton (57) ABSTRACT

A system for visualizing an anatomical target includes an imaging device (105) configured to collect real-time images of an anatomical target. A three-dimensional model (136) is generated from pre- or intra-operative images and includes images of structures below a surface of the anatomical target not visible in the images from the scope. An image processing module (148) is configured to generate an overlay (107) registered to the real-time images and to indicate the structures below the surface and a depth of the structures below the surface. A display device (118) is configured to concurrently display the real-time images and the overlay.

20 Claims, 7 Drawing Sheets

Related U.S. Application Data (60) Provisional application No. 61/935,643, filed on Feb. 4, 2014.

(51) Int. Cl.
*A61B 17/00* (2006.01)
*A61B 34/10* (2016.01)
*A61B 34/30* (2016.01)

(52) U.S. Cl.
CPC ...... *A61B 1/00165* (2013.01); *A61B 1/00194* (2022.02); *A61B 34/10* (2016.02); *A61B 90/361* (2016.02); *A61B 2017/00243* (2013.01); *A61B 2034/107* (2016.02); *A61B 34/30* (2016.02); *A61B 2034/301* (2016.02); *A61B 2090/3614* (2016.02); *A61B 2090/365* (2016.02)

(56) References Cited

U.S. PATENT DOCUMENTS

| | | | |
|---|---|---|---|
| 2008/0009895 A1 | 1/2008 | Pokomey et al. | |
| 2008/0207997 A1* | 8/2008 | Higgins | A61B 90/36 600/114 |
| 2009/0156895 A1* | 6/2009 | Higgins | G06T 19/003 600/117 |
| 2011/0234780 A1 | 9/2011 | Ito | |
| 2011/0237915 A1* | 9/2011 | Yamaguchi | G06T 7/0012 600/339 |
| 2011/0282151 A1 | 11/2011 | Trovato et al. | |
| 2012/0053434 A1 | 3/2012 | Saito | |
| 2013/0137926 A1* | 5/2013 | Itai | A61B 1/04 600/111 |
| 2013/0165948 A1 | 6/2013 | Popovic | |
| 2015/0141814 A1* | 5/2015 | Lee | G06T 7/62 600/425 |
| 2015/0146946 A1 | 5/2015 | Elhawary | |
| 2016/0038004 A1* | 2/2016 | Tanaka | A61B 1/000094 600/371 |

FOREIGN PATENT DOCUMENTS

| | | | | |
|---|---|---|---|---|
| WO | 2011102012 A1 | 8/2011 | | |
| WO | 2012035492 | 3/2012 | | |
| WO | 2012035492 A1 | 3/2012 | | |
| WO | WO-2012035492 A1 * | 3/2012 | ......... | A61B 1/00006 |
| WO | 2012156873 A1 | 11/2012 | | |
| WO | 2012172474 A1 | 12/2012 | | |
| WO | 2013061225 A1 | 5/2013 | | |
| WO | 2013093761 A2 | 7/2013 | | |

OTHER PUBLICATIONS

Zenbustsu, et al: "3D ultrasound assisted laparoscopic liver surgery by visualization of blood vessels", 2013 Joint UFFC, EFTF and PFM Symposium.
Hansen, et al: "Illustrative visualization of 3D planning models for augmented reality in livery surgery", International Journal of Computer Assisted Radiology and Surgery, Mar. 2010.
Hansen, et al: "Illustration of Vascular Structures for Augmented Reality in Liver Surgery", IFMBE Proceedings 25/IV, pp. 2113-2116, 2009.
Clinical User Guide; Revision 1.2, VectorVision cranial/ENT, Version 7.8, Copyright 2009.
Winne, et al: "Overlay visualization in endoscopic ENT surgery", International Journal of Computer Assisted Radiology and Surgery, vol. 6, May 2011.
Fusaglia, et al: "Endoscopic Image Overlay for the Targeting of Hidden Anatomy in Laparoscopic Visceral Surgery", Augmented Environments for Computer-Assisted Interventions, Lecture Notes in Computer Science 7815, 2013.
Noboyuki, et al: "Image-Guided neurosurgery system integrating AR-based navigation and open-MRI monitoring", Computer Aided Surgery, 10(2), vol. 10, No. 2, Mar. 2005.
Xiaochuan Sun: "Image Guided Interaction in Minimally Invasive Surgery", Master Thesis, Simon Fraser University, 2012.
Sebastian Vogt: "Real-Time Augmented Reality for Image-Guided Interventions", Doctor Thesis Universitat Erlangen-Numberg, 2009.
Nakamachi Eiji et al. "Development of Automatic 3D Blood Vessel Search and Automatic Blood Sampling Systemby Using Hybrid Stereo-Autofocus Method" Hindawi Publishing Corporation, International Journal of Optical, vol. 2012, Article ID 258626, 2012, 11 pages.
Zenbutsu, Satoki et al., "Development of Blood Vessel Depth Displaying Method for Laparoscopic Surgery Guidance", Journal of Medicine Imaging and Health Informatics, vol. 3, 2013, pp. 101-106.
Buczkowskim, Piotr et al., "Preoperative Doppler Ultrasound Examination of Saphenous Veins", Kardiochirurgia I Torakochirugia Polska, 2012, vol. 9, No. 2, pp. 175-181.
Szpala, Stainslaw et al., Real-Time Fusion of Endoscopic Views With Dynamic 3-D Cardiac Images: A Phantom Study, IEEE Transactions on Medical Imaging, vol. 24, No. 9, Sep. 2005.
Figl, Michael et al, "Image guidance for robotic minimally invasive coronary artery bypass", Computerized Medical Imaging and Graphics, vol. 34, 2010, pp. 61-68.
Van Ooijen, Peter M.A. et al., "Coronary Artery Fly-Through using Electro Beam Computer Tomography", Circulation Journal of the America Heart Association, 2000.

* cited by examiner

VISUALIZATION OF DEPTH AND POSITION OF BLOOD VESSELS AND ROBOT GUIDED VISUALIZATION OF BLOOD VESSEL CROSS SECTION

CROSS-REFERENCE TO RELATED APPLICATIONS

This application is a continuation application of U.S. application Ser. No. 15/115,846, filed on Aug. 1, 2016, which is a U.S. National Phase application under 35 U.S.C. § 371 of International Application No. PCT/IB2015/050551 filed Jan. 26, 2015, which claims the benefit of U.S. Application No. 61/935,643 filed on Feb. 4, 2014, the contents of which are herein incorporated by reference.

BACKGROUND

Technical Field

This disclosure relates to medical instruments and methods and, more particularly, to systems and methods for improved visualization and guidance for internal anatomy in medical applications.

Description of the Related Art

Coronary artery bypass grafting (CABG) is a surgical procedure for revascularization of obstructed coronary arteries. In conventional surgery, the patient's sternum is opened, and the heart is fully exposed. However, minimally invasive (MI) bypass surgery is performed through small ports between the ribs. An important part of a CABG procedure is the removal of a vessel from the patient's body, which is then used to bypass one or more atherosclerotic narrowings in the coronary arteries. The vessel most commonly removed and used is an Internal Mammary Artery (IMA), which may include a Left IMA (LIMA) or Right IMA (RIMA), which are located in the thoracic cavity.

During MI cardiac bypass surgery, direct access to these IMA vessels is not available, and they are removed using long instruments inserted into ports through intercostal muscles in spaces between the ribs. During MI surgery, a surgical assistant can hold the endoscope, or it can be held using robotic guidance. In the case of robotic guidance, visual servoing can be used to move the robot to a specific location. Visual servoing consists of selecting a point on the endoscope image, with the robot moving in such a way that the point becomes located in the center of the image.

Endoscope images are the only visualization method for this type of procedure, but the endoscope provides only a limited view of a small segment of a blood vessel. For MI surgery, a surgeon works with elongated instruments inserted between the ribs reaching below the sternum area. Localization of arteries in endoscopy images and manipulation of the endoscope is one of the main problems limiting wide acceptance of minimally invasive coronary bypass grafting surgery. Some of the arteries can be covered with tissue. The surgeon removes the tissue intra-operatively to access the vessel. A lack of depth perception requires the surgeon to use extreme caution when removing tissue located directly above or on top of the vessel to ensure safe exposure of the vessel. This increases procedure time and is an important stress point for the surgeon. In minimally invasive CABG, the problem is amplified because surgeons cannot palpate the heart surface. The length of instruments used in minimally invasive CABG does not permit any tactile feedback on the proximal end of the tool.

SUMMARY

In accordance with the present principles, a system for visualizing an anatomical target includes an imaging device configured to collect real-time images of an anatomical target. A three-dimensional model is generated from pre- or intra-operative images and includes images of structures below a surface of the anatomical target not visible in the images from the imaging device. An image processing module is configured to generate an overlay registered to the real-time images and to indicate the structures below the surface and a depth of the structures below the surface. A display device is configured to concurrently display the real-time images and the overlay.

A system for visualizing an anatomical target includes an imaging device configured to collect real-time images of an anatomical target. A three-dimensional model is generated from pre- or intra-operative images and includes images of structures below a surface of the anatomical target not visible in the images from the imaging device. An image processing module is configured to generate an overlay, which is registered to the real-time images and indicates the structures below the surface. A visualization feature is configured to display an internal view of at least a portion of the structures below the surface. A display device is configured to concurrently display at least two of: the real-time images, the overlay or the internal view.

A method for visualizing an anatomical target includes imaging an anatomical target using a scope to collect real-time images; registering the real-time images with a three-dimensional model of an internal volume of the anatomical target; displaying the real-time images with an overlay registered to the real-time images; and indicating structures below the surface of the anatomical target and a depth of the structures below the surface on the overlay.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, systems and methods are provided to compute and visualize depth of a blood vessel relative to an endoscope view or relative to a surgical instrument. Alternative methods for visualization of the depth overlaid on images of the vessels may include color gradients and other visual indications. Inspection of a blood vessel, e.g., a coronary artery, may be implemented by guiding a robotically manipulated endoscope along the blood vessel, or visualizing an image of a heart surface and performing a virtual fly-through three-dimensional (3D) visualization simultaneously. This brings all the diagnostic and anatomical information from pre-operative 3D images into an intervention. In hybrid revascularization, this method can be used to visualize where stents will be located and plan a bypass such that there is minimal incidence on the planned or existing stenting sites.

Providing information on position of a blood vessel relative to the endoscope view has been attempted, such attempts have not obtained information and visualization of the depth of vessels with respect to a surface of the organ (e.g., a heart). Depth of the vessels can be important information allowing a surgeon to decide what part of the vessel they will use for the bypass location and to decide what surgical instrument to use to remove the excess tissue above the blood vessel.

In one embodiment, a system and method compute and visualize the depth of blood vessels relative to the surface of an organ. This permits improved planning of surgical procedures (e.g., coronary bypass) and increases safety by reducing the risk of damaging the vessel through removal of the excess tissue. One application includes coronary artery bypass surgery to visualize position of a harvest artery (LIMA) and of target arteries (coronary arteries).

In another embodiment, during a minimally invasive cardiac bypass procedure, a diagnostic virtual fly-through visualization of a blood vessel or vessels, e.g., coronary arteries, along with the endoscope view is employed to choose a site of a bypass. This may result in selection of the site to avoid lesions or other features with a potential strong impact on surgical outcomes. The present principles permit inspection of a coronary artery by: guiding a robotically manipulated endoscope along the artery, visualizing an image of the heart surface and a virtual fly-through 3D visualization concurrently. This brings all the diagnostic and anatomical information from the pre-operative 3D images into the intervention. During the diagnostic stage, methods to generate a fly through 3D visualization of an artery to inspect for branching and stenosis are generated by using a camera view from inside the three-dimensional vessel. Methods to generate a fly-through from electron beam computer tomography, etc. may be employed. The fly-through improves the diagnostic value of 3D imaging allowing a closer inspection of the arteries and the plaque inside the vessel.

It should be understood that the present principles will be described in terms of medical instruments for use with and for a coronary bypass procedure; however, the teachings of the present invention are much broader and are applicable to any instrument or procedure where enhanced visualization of a target anatomy is needed or desired. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
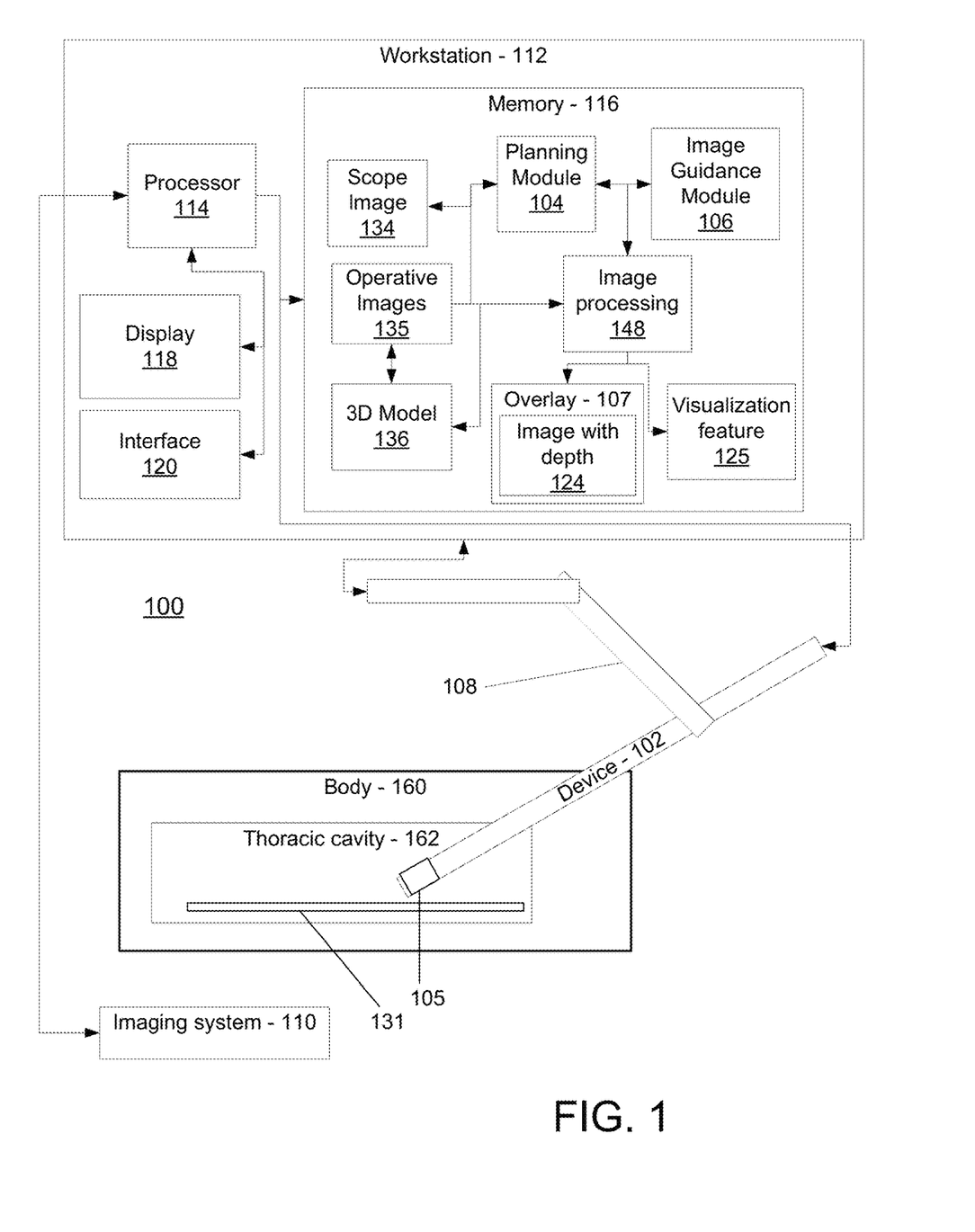
FIG. 1 is a block/flow diagram showing a system for visualizing an anatomical target in accordance with one embodiment.

Referring now to the drawings in which like numerals represent the same or similar elements and initially to FIG. 1, a system 100 for minimally invasive surgery is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store a planning module 104 and an image guidance module 106 employed to work in conjunction with a medical device 102. The medical device 102 may include an imaging device 105 (e.g., camera, fiber optics with lens, etc.) that may be deployed with one or more of a catheter, a guidewire, a probe, an endoscope, a flexible endoscope, a robot, an electrode, a filter device, a balloon device, or other medical component, etc. The device 102 may be inserted into a body 160 of a patient. In one embodiment, a procedure to be performed may include minimally invasive coronary surgery, and the device 102 may be inserted into a thoracic cavity 162 of the body 160 to observe, define and/or isolate an anatomical target 131, such as a blood vessel (e.g., an internal mammary artery (IMA)).

The planning module 104 includes the following elements and features. During, e.g., a vessel take-down for a coronary bypass procedure, the planning module 104 plans for the control of visualization of a target vessel to be harvested, e.g., the IMA, while permitting a surgeon to manipulate other instruments. The planning module 104 stores a plan for manipulating a robot or robot system 108 or providing guidance to an operator during a manual procedure.

An image processing module 148 controls visualization, depth indications, etc. to provide a comprehensive field of view, and to further provide image registration permitting overlaying of preoperative (or intra-operative) images on, e.g., an endoscope video using methods known in art. The planning module 104 provides for the selection of target points of interest, which can be referred to or indexed for use with the image guidance module 106. The planning module 104 also provides for computation of blood vessel or other anatomical feature dimensions (e.g., depths, etc.).

The image processing module 148 may be employed to register and overlay operative images 135, such as preoperative or intraoperative images taken using an imaging device 110. The imaging device 110 may be employed contemporaneously or at another time and location to collect the images. The operative images 135 may include three dimensional preoperative computed tomography (CT) images or magnetic resonance images (MRI), etc. or intra-operative X-rays or ultrasound. Other imaging modalities are also contemplated. The operative images 135 are employed to build a three-dimensional model 136 including virtual internal cross-sections or internal view images along the anatomical target 131.

The image guidance module 106 provides image-based control of the device 102, e.g., an endoscope, preferably by controlling the robot system 108, which supports the device 102. An overlay 107 may be generated using the image processing module 148 and/or the planning module 104. The overlay 107 may include a current live endoscope image 134 with highlighted regions representing a blood vessel image 124 visualized thereon. The image 124 may be coded, colored or textured to visually provide additional information to a user, such as, e.g., a depth below a surface that the blood vessel exists at, etc.

The image guidance module 106 may be employed to guide the robot system 108 along the length of the target anatomy 131. In one embodiment, the device 102 is guided using the points of interest assigned during a planning stage that are stored in a plan for use by the planning module 104.

Workstation 112 includes a display 118 for viewing internal images of a subject (patient) or volume and may include images with an overlay or other rendering generated over images collected from the device 102. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

The operative images 135 of the anatomical target 131 may include 3D images of the blood vessel, including coronary arteries, etc. During a diagnostic or preoperative scan of the patient anatomy, a 3D angiographic scan may be acquired. From the scan, a 3D model 136 of the target 131 can be constructed. For example, from the scanned image, a segmentation method, which may include a method known in the art, can be employed to generate a 3D surface of the target, with all its branches and features. Next, virtual angiography images are generated or obtained from a camera viewpoint inside the vessel. The generation of virtual images may include a detection of the centerline of the vessel structure. The centerline can be computed using skeletonization, which finds a line in the center of vessels while minimizing distance from the line to the vessel walls. This method is well-suited to the applications in accordance with the present principles since one purpose is to show spatial branching of the vessel.

Then, registration of the 3D model 136 with the real-time endoscopic images is performed. With the endoscope 102 in place and located to view an organ, e.g., the heart, surgeon can start the acquisition of endoscopic images. To do so, the surgeon or a robot 108 moves the endoscope 102 using uncalibrated robotic visual servoing or other technique along the visible portion of the target 131. The surgeon may select points along a blood vessel or other path to move the endoscope 102 accordingly. The surgeon can also use a surgical instrument as a guide, as the instrument moves, and the endoscope 102 can follow the tool tip.

To register the operative images 135 and/or the 3D model 136 to the endoscope images, matching algorithms stored in the image processing module 148 may be employed. Other image processing techniques may also be employed to register and maintain registration of the images/models.

The endoscope 102 may be flexible and can be either or both of oblique and forward viewing. The motion of endoscope 102 may be pre-programmed and gated by the image processing module 148. In this embodiment, the motion is generated and gated by the surgeon's commands.

In accordance with particularly useful embodiments, the operative images (pre-operative or intra-operative) 135 and/or 3D model(s) 136 may be employed to determine an internal anatomy of an organ that is not visible in an external camera view, e.g., collected by the endoscope camera 105. In one example, a heart may include blood vessels below a surface thereof that may need to be identified, bypassed, etc. The overlay image 107 may be generated to include positions and sizes of the blood vessel that are not visible in the image 134. The scope images 134 are registered with the operative images (pre-operative or intra-operative) 135 and/or 3D model(s) 136 so that identified blood vessels may be rendered in the overlay image 107. The overlay 107 reveals internal structures within the anatomical target 131. This may include the generation of a cross-sectional image at a position of the endoscope 102, at a point selected by an operator, etc. In one embodiment, the overlay 107 may include colors, textures or other visual information to indicate a depth of the blood vessel below the surface or other information. For example, based upon the operative images 135, an amount of plaque build-up within the vessels may be known and could be displayed in the overlay 107 at the corresponding depth positions.

Points of interest may be selected and indicated in the image overlay 107. Once selected on the image 134 of the target 131, a cross-sectional view of the selected point may be generated and displayed. The points of interest can be stored and referred to during the procedure. Alternately, as the points are selected, the robot 108 (endoscope holder) can move the endoscope 102 to that location (e.g., joint positions of the robot 108 may be stored, so they can be referred to during an image guided portion of the procedure).

The selection of points on the anatomical points of interest may include, e.g., an initial point, an end point and other anatomical features or points. The overlay 107 may include real-time images 134 and a map or generated visual display generated using image processing 148 to indicate the location of blood vessels and features (e.g., bifurcations) that are not directly visible on the endoscope images, as they could be located underneath fascia and other tissue. A 3D visualization feature 125 generates an internal view (e.g., cross section of the vessel or a fly-through image or video) at a selected position or points on a structure. The internal data is reproduced virtually using the 3D model 136 and/or the 3D images 135. The internal view may be provided alone or with other views for display to a user/surgeon. The internal view may be generated automatically or by user command. For example, a cross section may be viewed concurrently with and endoscope image to show the presence of any calcifications or atherosclerotic narrowings within a blood vessel.

Figure 2:
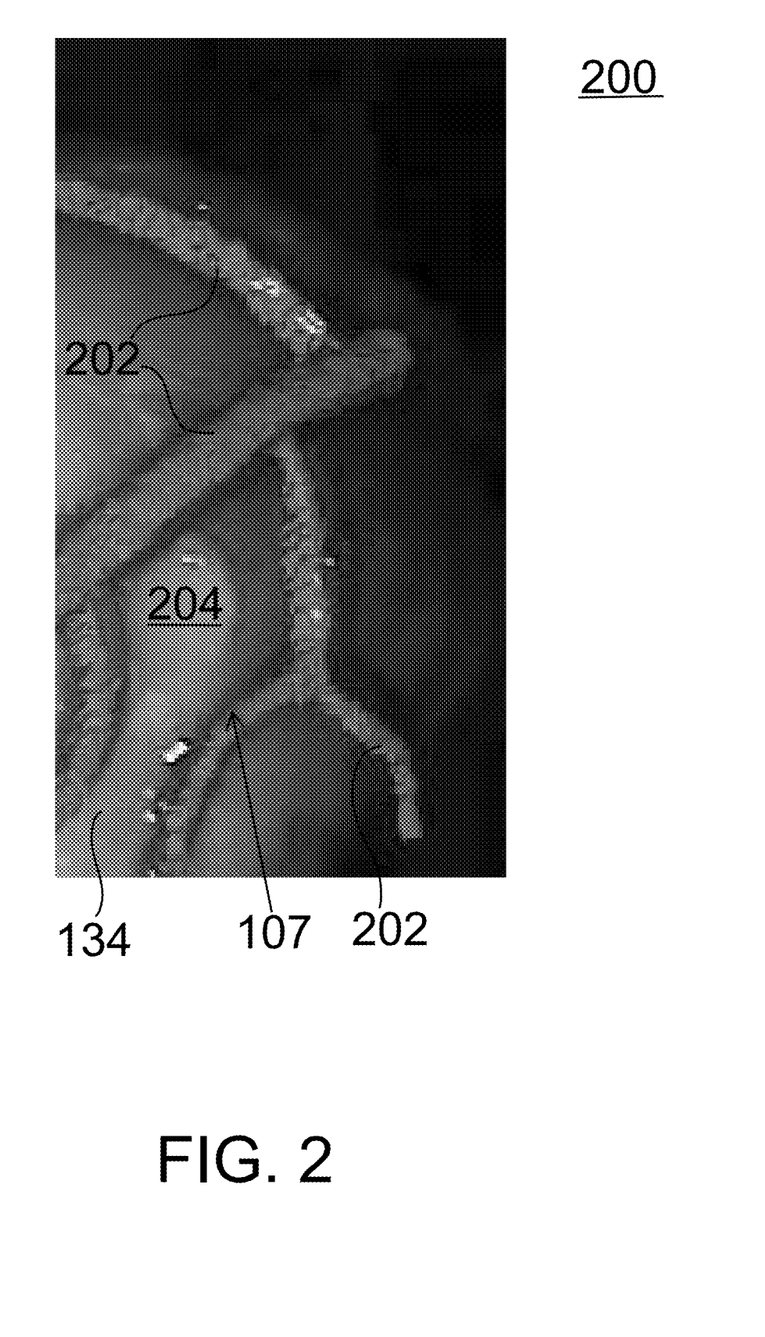
FIG. 2 is an endoscope image having an overlay showing blood vessels below the surface of a heart in accordance with the present principles.

Referring to FIG. 2, an image 200 shows an overlay 107 of blood vessels 202 (e.g., arteries) from pre-operative/intra-operative 3D images over an endoscope image 134. The image 200 indicates depth of blood vessels 202 relative to the surface of an organ 204 (the heart in this example). The indication of depth permits improved planning for surgical procedures (e.g., coronary bypass) and increases safety by reducing the risk of damaging the vessel or vessels during removal of the excess tissue over the blood vessels 202 during surgery. Image 200 shows a map of coronary arteries 202. The coronary arteries 202 may be textured, colored, spatially oriented, sized or labeled with alphanumeric characters to indicate properties of the arteries, such as depth from the surface, locations of lesions or other features, blockages, etc. One application where image 200 is useful includes coronary artery bypass surgery to visualize a position of a harvest artery (e.g., a left internal mammary artery (LIMA)) and of target arteries (coronary arteries).

As described above, registration between endoscope images 134 and preoperative/intraoperative images 135 or 3D models 136 is achieved for the heart and blood vessels. The overlay 107 is generated to indicate the properties that are to be conveyed visually to the user on a display. This is provided in accordance with one illustrative embodiment described hereinafter.

Figure 3:
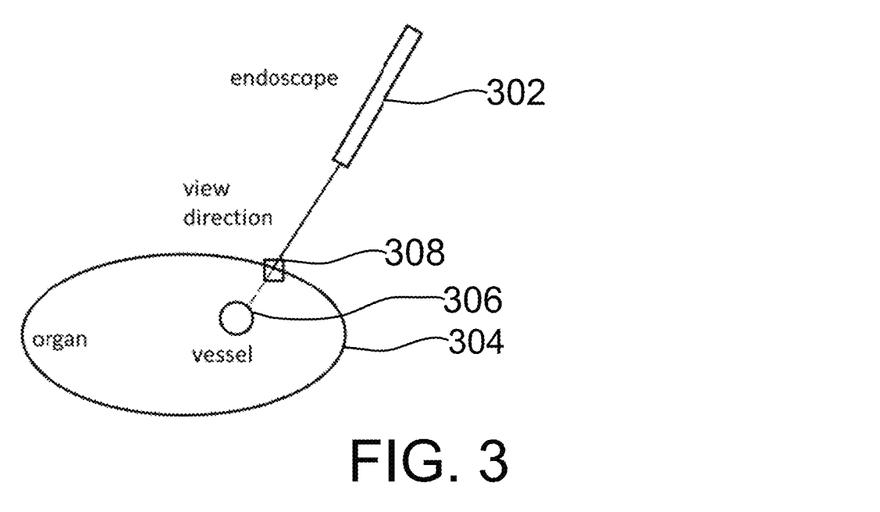
FIG. 3 is a schematic diagram showing an endoscope view direction for defining a depth of a vessel below a surface in accordance with the present principles.

Referring to FIG. 3, a schematic diagram shows an optical imaging system 302, an organ surface (heart) 304 and a hidden blood vessel 306. A direction of view 308 is determined for the instruments of the imaging system 302. The result of 2D-3D registration includes a position and orientation of the endoscope 102 with respect to a 3D coordinate system of a preoperative image (135). The exact 'depth', i.e., the distance between the endoscope 102 and the heart 304 may not be known, since the endoscope 102 is not calibrated. However, a view direction 308 can be computed from a transformation matrix of the 2D-3D registration, using mathematical formulas known in art.

Figure 4:
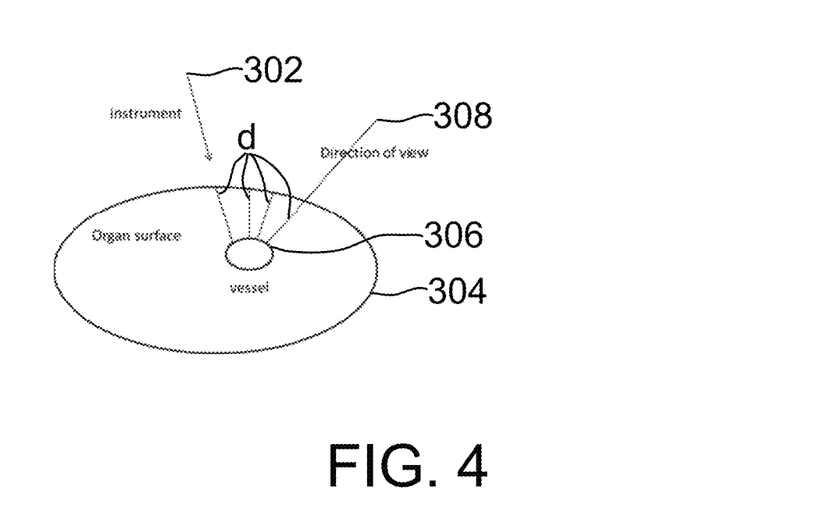
FIG. 4 is a schematic diagram showing different possible views for defining a vessel below a surface in accordance with the present principles.

Referring to FIG. 4 with continued reference to FIG. 1, a depth of the vessel 306 is computed and defined. In general, the depth of the vessel is not uniquely defined, and depends on a reference object from which the depth "d" is being computed (e.g., the direction of view 308 of the endoscope, the instrument direction, the surface of the heart 304, etc.). For example, the depth d can be defined as the closest distance to the organ surface, or the distance along the direction of view 308. In one embodiment, since the endoscope 302 provides the only visual feedback of the operating field, the depth d may be measured from the direction of view 308 of the endoscope 302. In another embodiment, the distance d between the instrument positioned above the vessel or immediately on the surface of the heart can be employed. In one embodiment, the surgeon uses the overlay 107 of the endoscope image and operative (image 202) to guide the instrument to a location on the heart 304. Using image recognition methods known in art, the system 100 detects a position of the instrument 302 in the image 134 (e.g., since the instrument 302 has a significantly different color than the rest of the heart or organ, or a well-defined shape that is easily identified). A simple color thresholding method may be employed to identify the instrument 302, although other methods may be employed. Using the image registration, a point on the heart surface of the 3D image is identified from the instrument tool tip. The depth is then defined as the distance from that point to the closest point on the blood vessel. Depth can also be computed from this point to other points on the vessel structure. The depth information can then be visualized on the live endoscope images 134.

Figure 5:
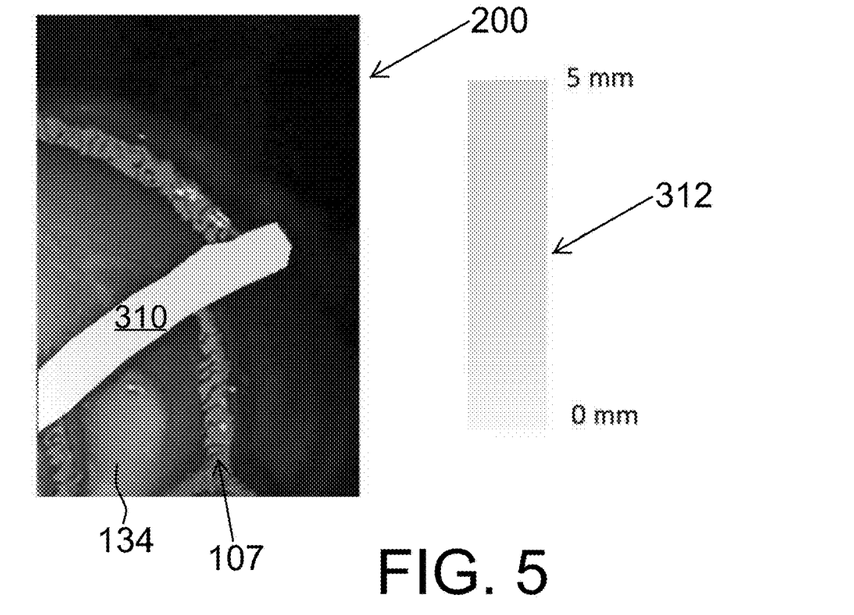
FIG. 5 is an endoscope image having an overlay with a portion coded to indicate a depth of a blood vessel below the surface of a heart and having a color gradient scale in accordance with the present principles.

Referring to FIG. 5, for illustrative purposes, assume that a main vessel 310 located in the middle of the image 200 is intramyocardial at the proximal end and resurfaces at the distal end of the vessel in the image 200, i.e., the depth of the vessel 310 is deeper at the right end of the image 200. After the distance of the each segment of the vessel is computed, a gradient 312 may be applied to show the depth based on, e.g., color. Other indicators, e.g., other than color encoding through gradients, may also be employed to represent depth, such as using higher or lower density lines inside the vascular structure which are closer together as the depth is greater, etc.

Figure 6:
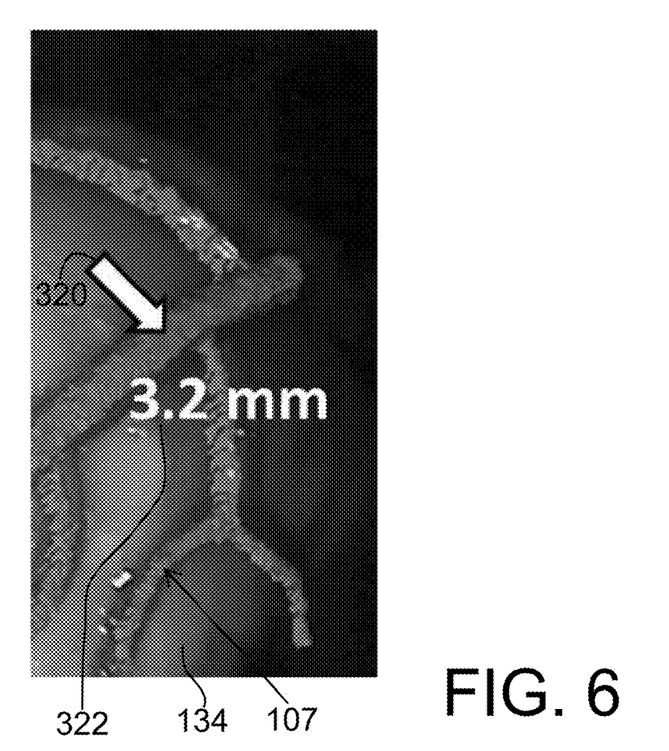
FIG. 6 is an endoscope image having an overlay showing blood vessels below the surface of a heart and showing a cursor for pointing to a portion of the blood vessel to indicate a depth of the blood vessel below the surface of the heart at the cursor location in accordance with the present principles.

Referring to FIG. 6, in another embodiment, the depth can be indicated using a cursor 320 or overlay information (e.g., alphanumeric characters) 322 as a cursor or pointer is located at different points on the vessel.

Figure 7:
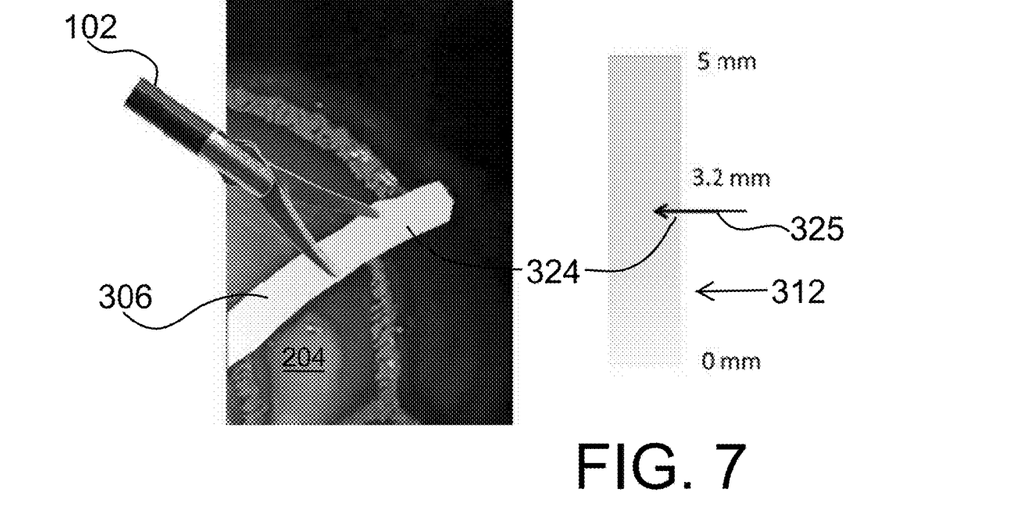
FIG. 7 is an endoscope image having an overlay showing blood vessels below the surface of a heart and showing a portion of the blood vessel near a tool tip having a depth of the blood vessel below the surface of the heart indicated and further showing a gradient key with an arrow indicating a depth near the tool tip in accordance with the present principles.

Referring to FIG. 7, another embodiment can indicate the depth as a depth under the instrument 102 (or any designated instrument). As the instrument 102 is located over the blood vessel 306, a depth 324 is indicated between a surface of the organ 204 and the blood vessel 206 at the location of the instrument 102. The instrument 102 need not be an endoscope or the imaging device collecting the images. The depth may be indicated with or without color or other indicators. The depth 324 may be indicated with a color gradient 312 along with an indicator 325 (e.g., an arrow, etc.) showing a specific depth at or near the tool tip of instrument 102.

Figure 8:
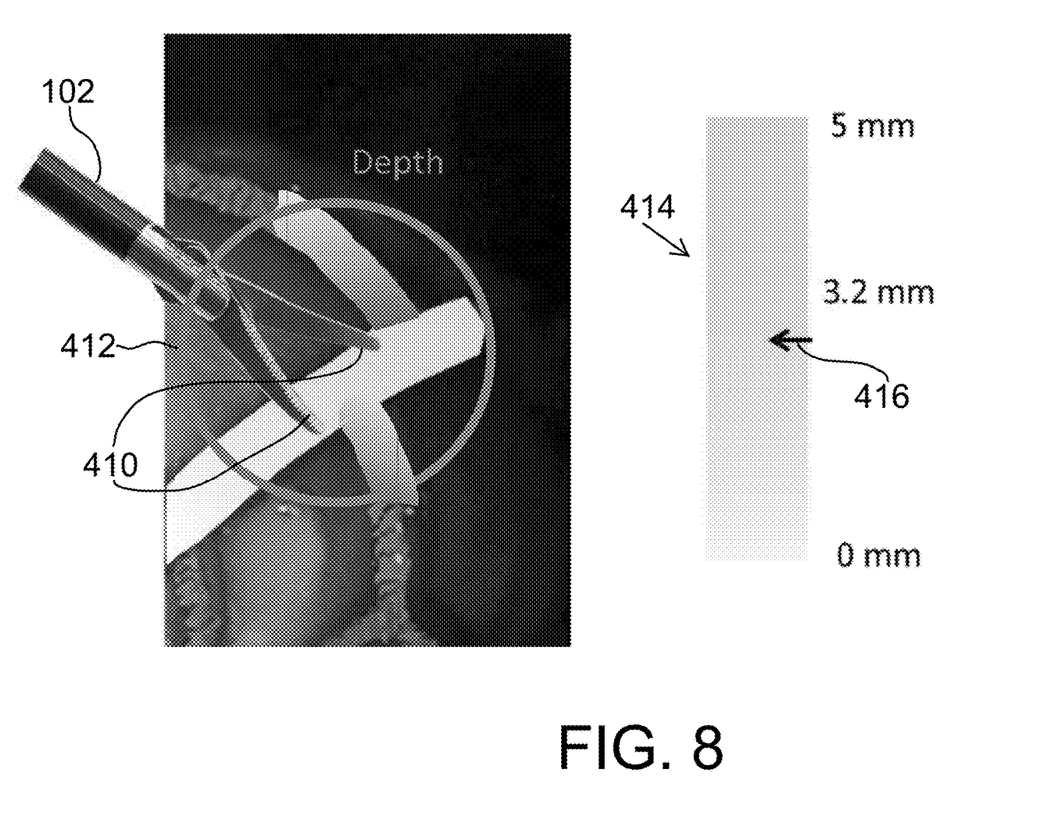
FIG. 8 is an endoscope image having an overlay showing blood vessels below the surface of a heart and showing a shaped region around a tool tip wherein a depth of the blood vessels below the surface of the heart within the shaped region are indicated and further showing a gradient key with an arrow indicating the depth within the region in accordance with the present principles.

Referring to FIG. 8, in another embodiment, an instrument tip 410 can be continuously tracked, and the depth from the tool tip 410 to all vascular structures within a user defined region 412, e.g., a radius or other shaped region in the vicinity of the tip, can be color encoded using a gradient 414. The depth 324 may be indicated with the color gradient 414 along with another indicator 416 (an arrow, etc.) showing a specific depth at or near the tool tip of instrument 102.

While the present principles have been described with reference to heart related surgery and, in particular, coronary artery bypass grafting, it should be understood that the present principles are applicable to other situations where endoscopic surgery is performed on blood vessels (thoracoscopy or general laparoscopy) or other anatomical structures during an intervention.

Referring again to FIG. 1, embodiments may permit the inspection of a coronary artery by guiding a robotically manipulated endoscope 102 along a blood vessel (e.g., artery) using the overlay 107 and/or selected points of interest. In one embodiment, an image of the heart surface is visualized, and a virtual fly-through 3D visualization of interior anatomy (e.g., inside the blood vessels) or cross-sectional images can be concurrently visualized. The virtual fly-through 3D visualization of interior anatomy or cross-sectional images can be generated based upon the pre- or intra-operative 3D images 135 or models 136. The overlay 107 employs all the diagnostic and anatomical information from the pre- or intra-operative 3D images 135 or models 136 to be provided to the user during an intervention.

The system 100 may include the robot 108, which preferably includes at least two degrees of freedom to permit motion of the endoscope 102 in pitch and yaw around an insertion point in the chest or other area of the body. A relationship between the endoscope view and the preoperative/intraoperative 3D image can be established as described above. The relationship between the endoscope 102 and a robot coordinate system (e.g., robot base) is known from robot kinematics and encoders.

Figure 9:
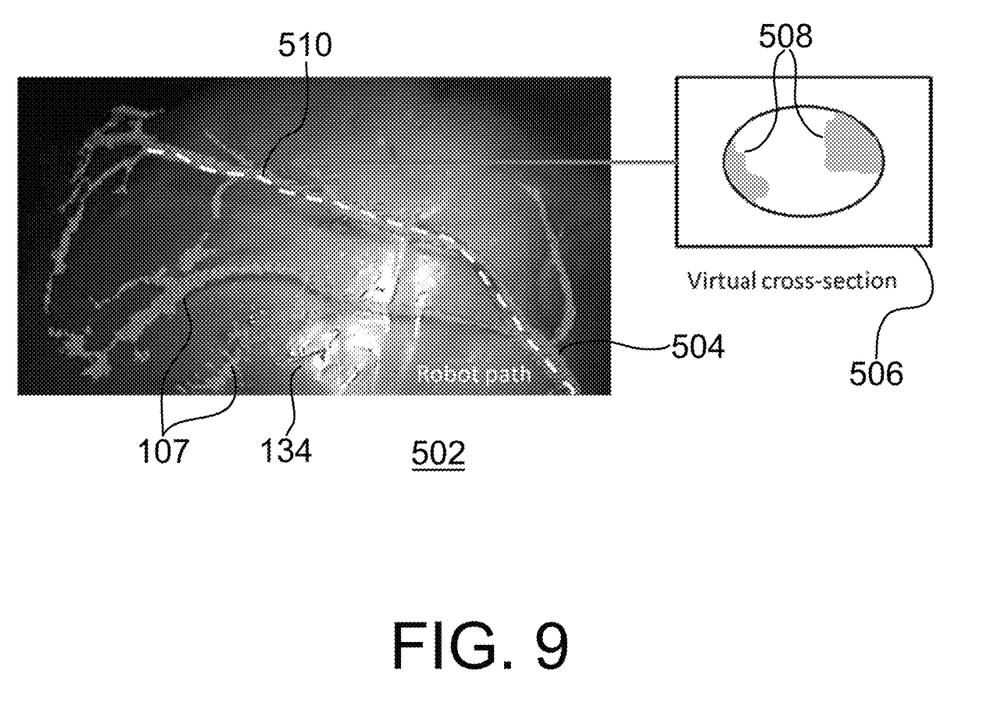
FIG. 9 is an endoscope image having an overlay showing blood vessels below the surface of a heart and showing a path along a blood vessel to be followed using robot guidance to view internal structures of the blood vessel using 3D fly-through images or a cross-section at an indicated position in accordance with the present principles.

Referring to FIG. 9 with continued reference to FIG. 1, an image 502 shows an endoscope image 134 having an overlay 107 registered thereon based upon operative images 135 and/or model(s) 136. A surgeon selects a coronary artery 504 or a portion thereof in the endoscope view. The robot 108 (FIG. 1) moves the endoscope 102 along the selected artery 504 using the known spatial relationships between the robot 108 and an image (heart) coordinate system (e.g., coordinate system of the 3D scanning device (used to generate images 135)). A 3D visualization feature 125 (FIG. 1) generates a cross section 506 (or three-dimensional fly-through images) of the vessel at a selected position or positions that can be provided for display to a user/surgeon.

For example, the cross section 506 may show a virtual image 508 showing the presence of any calcifications or atherosclerotic narrowings.

In another embodiment, automatic visualization may be employed and controlled by the positioning of the endoscope 102 or other device. For example, the vessel cross section 506 may be rendered for a position corresponding to a center of the endoscope image 134, or at a selected position, etc. The cross-section image includes a virtual image 508 that can be automatically selected. The cross section 3D view 506 can be generated and visualized by the surgeon.

In another embodiment, robotic guidance of the endoscope along a path 510 or blood vessel may be provided with visualization of the corresponding cross section 506. The vessel cross section 506 at the center of the endoscope image 134 can be automatically selected, and the cross section 3D view can be generated and visualized by the surgeon. Based on the known values of the robot encoders associated with every position in the image, the robot 108 can move the endoscope 102 to follow the path 510 over its length at a velocity defined by the user. As the endoscope 102 moves, both the image of the endoscope 134 as well as the virtual image 508 reconstruction can be concurrently shown on the display 118. The image guidance module 106 is employed to guide the endoscope 102. The surgeon can automatically locate the endoscope at a location by using visual servoing and/or referring to previously selected points, e.g., selected during planning. As the surgeon progresses along the path 510 (e.g., artery), both a current endoscope view (scope image 134), the overlay 107 (with or without computed depth data) and a selected cross-section 506 may be displayed concurrently to the surgeon. The interior camera view or cross-section 506 is provided from the preoperative images 135 and/or model 136. As the motion of the endoscope 102 is known from robot encoders combined with the registration information, the path 510 can be followed closely and accurately and generate a fly-through video of the interior of the artery 504 as the robot 108 moves along the path 510.

The present method also can be employed in hybrid revascularization to visualize where stents will be located (using cross sections (506) for neighboring arteries) and plan the bypass such that there is minimal incidence on the stenting sites.

Other applications for endoscopically-guided minimally invasive surgery may include cardiac surgery, such as minimally invasive coronary artery bypass grafting, atrial septal defect closure, valve repair/replacement, etc.; laparoscopic surgery, such as hysterectomy, prostatectomy, gall bladder surgery, etc.; natural orifice transluminal surgery (NOTES); pulmonary/bronchoscopic surgery; neurosurgical interventions; etc.

Figure 10:
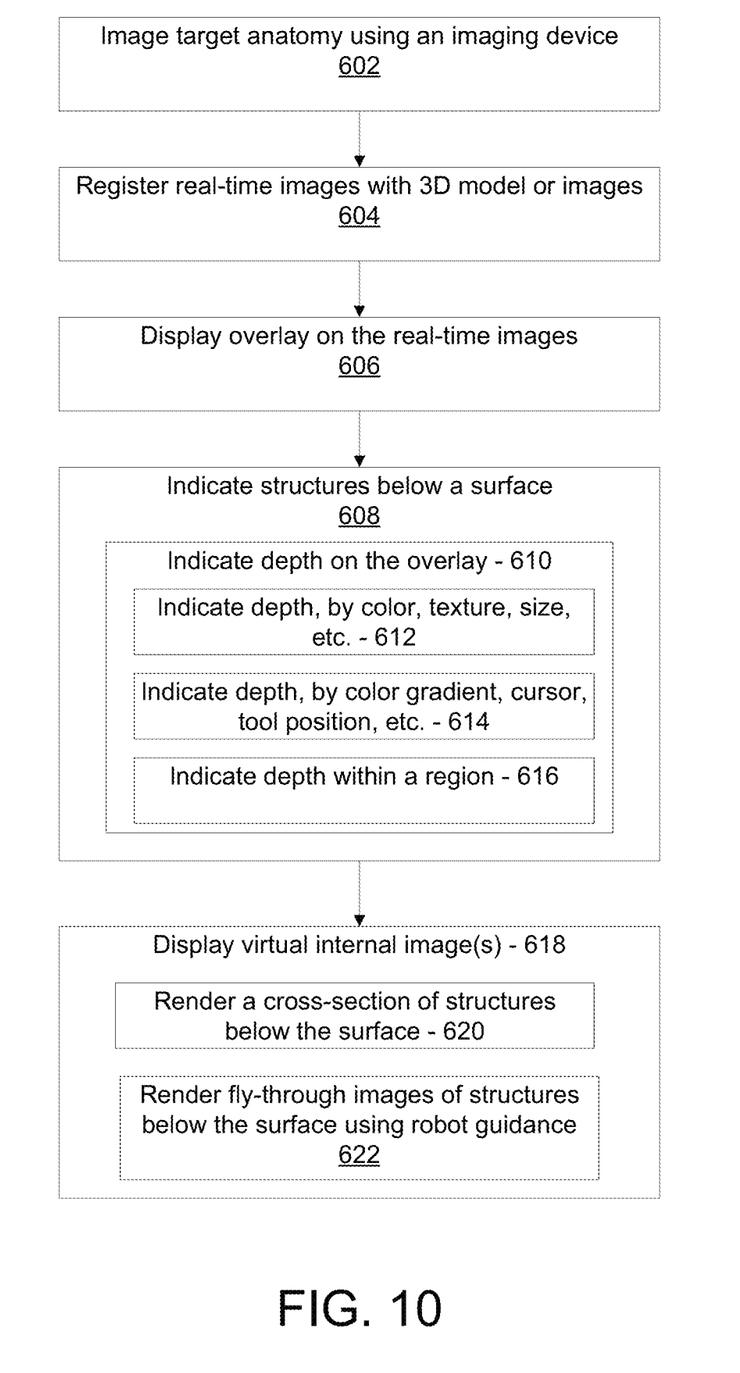
FIG. 10 is a flow diagram showing a method for visualizing an anatomical target in accordance with illustrative embodiments.

Referring to FIG. 10, a flow diagram shows a method for visualizing an anatomical target in accordance with the present principles. In block 602, an anatomical target is imaged using an imaging device (e.g., a scope) to collect real-time images. In block 604, the real-time images are registered with a three-dimensional model of an internal volume of the anatomical target. In block 606, the real-time images are displayed with an overlay registered to the real-time images. In block 608, structures below the surface of the anatomical target are indicated.

In block 610, a depth of the structures below the surface is indicated on the overlay. In block 612, the depth may be indicated by one of color, texture, size of the structures rendered, etc. in the overlay. In block 614, the depth is indicated by one or more of a color gradient where color intensity is proportional to depth; a relative position of a tool in the real-time images; or a cursor over the overlay to generate an alphanumeric label indicating the depth. In block 616, the depth of the structures below the surface is indicated within a shaped area of a tool tip, e.g., within a circle or rectangle.

In block 618, a virtual image showing an internal view of the structures below the surface may be displayed. In block 620, the internal view includes a cross-sectional view of the structures below the surface. The cross-sectional view may be rendered by selecting a point on the structure (e.g., using a cursor, using a tool, using a scope image (where an image center or other position selects the point), etc. In block 622, a robot may be guided along a path corresponding to at least one of the structures below the surface, wherein the internal view includes three-dimensional fly-through images of the structures below the surface.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for visualization of depth and position of blood vessels and robot guided visualization of blood vessel cross section (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for visualizing an anatomical target, the system comprising:

an imaging device configured to collect real-time images of an anatomical target;

a three-dimensional (3D) model generated from pre-operative images or intra-operative images and including images of at least one structure located below a surface of the anatomical target, such that the at least one structure is not visible in the real-time images from the imaging device;

an image processor configured to generate an overlay registered to the real-time images which display the at least one structure located below the surface of the anatomical target and indicates a depth of the at least one structure below the surface of the anatomical target;

an image guidance processor configure to robotically guide the imaging device to locations along a path corresponding to the at least one structure located below the surface of the anatomical target, wherein, as the imaging device is robotically guided to a location along the path, the image processor is configured to display an internal view of a portion of the at least one structure corresponding to the location of the guided imaging device along the path; and a display device configured to concurrently display the real-time images, the internal view, and the overlay.

2. The system as recited in claim 1, wherein the image processor is further configured to indicate the depth of the at least one structure located below the surface of the anatomical region by one of color, texture, or size in the overlay.

3. The system as recited in claim 1, wherein the image processor is further configured to indicate the depth of the at least one structure located below the surface of the anatomical region by a color gradient presented with color intensity proportional to depth.

4. The system as recited in claim 1, wherein the image processor is further configured to indicate the depth of the at least one structure located below the surface of the anatomical region relative to a position of a tool in the real-time images.

5. The system as recited in claim 1, wherein the image processor is further configured to, in response to a cursor over the overlay, indicate the depth of the at least one structure located below the surface of the anatomical region by an alphanumeric label indicating the depth.

6. The system as recited in claim 1, wherein the image processor is further configured to indicate the depth of the at least one structure located below the surface of the anatomical region within a shaped area in a vicinity of a tool tip.

7. The system as recited in claim 1, wherein the image processor is further configured to generate a virtual image showing the internal view of the portion of the at least one structure located below the surface of the anatomical region.

8. The system as recited in claim 1, wherein:

the image processor is further configured to generate the internal view as at least one of (i) a virtual 3D fly-through image of the portion of the at least one structure located below the surface of the anatomical region or (ii) a virtual 3D cross-section image of the portion of the at least one structure located below the surface of the anatomical region; and the display device is further configured to display (i) the virtual 3D fly-through image of the portion of the at least one structure located below the surface of the anatomical region and (ii) the virtual 3D cross-section image of the portion of the at least one structure located below the surface of the anatomical region.

9. The system as recited in claim 1, wherein:

the image processor is further configured to:

receive a selection of a point on the at least one structure located below the surface of the anatomical region, and generate an internal view of the at least one structure at the selected point based on the 3D model that includes at least one of (i) a virtual 3D fly-through image of the at least one structure at the selected point and (ii) a virtual 3D cross-section image of the at least one structure at the selected point; and the display device further configured to display the internal view of the at least one structure at the selected point.

10. The system as recited in claim 1, wherein the anatomical target is an organ in a subject.

11. The system as recited in claim 1, wherein the at least one structure is at least one blood vessel.

12. The system as recited in claim 1, wherein the image processor is further configured to indicate the depth of the at least one structure located below the surface of the anatomical region relative to a position of a tool in the real-time images, wherein the tool is not the imaging device.

13. The system as recited in claim 1, wherein the depth is depth under a current position of the imaging device.

14. The system as recited in claim 1, further comprising a robot and wherein the image guidance processor is further configured to control the robot to robotically guide the imaging device along the path corresponding to the at least one structure located below the surface of the anatomical target.

15. A method for visualizing an anatomical target, comprising:
   collecting, by an imaging device, real-time images of an anatomical target;
   providing a three-dimensional (3D) model generated from pre-operative images or intra-operative images and including images of at least one structure located below a surface of the anatomical target, such that the at least one structure is not visible in the real-time images from the imaging device;
   generating an overlay registered to the real-time images which display the at least one structure located below the surface of the anatomical target and indicates a depth of the at least one structure below the surface of the anatomical target;
   robotically guiding the imaging device to locations along a path corresponding to the at least one structure located below the surface of the anatomical target,
   wherein, as the imaging device is robotically guided to a location along the path, the image processor is configured to display an internal view of a portion of the at least one structure corresponding to the guided location of the imaging device along the path; and
   concurrently displaying the real-time images, the internal view, and the overlay.

16. The method as recited in claim 15, further comprising indicating the depth of the at least one structure located below the surface of the anatomical region relative to a position of a tool in the real-time images, wherein the tool is not the imaging device.

17. The method as recited in claim 15, wherein the depth is depth under a current position of the imaging device.

18. The method as recited in claim 15, further comprising:
   generating the internal view as at least one of (i) a virtual 3D fly-through image of the portion of the at least one structure located below the surface of the anatomical region and (ii) a virtual 3D cross-section image of the portion of the at least one structure located below the surface of the anatomical region; and
   displaying (i) the virtual 3D fly-through image of the portion of the at least one structure located below the surface of the anatomical region and (ii) the virtual 3D cross-section image of the portion of the at least one structure located below the surface of the anatomical region.

19. The method as recited in claim 15, wherein the depth of the at least one structure located below the surface of the anatomical region is indicated relative to a position of a tool in the real-time images.

20. The method as recited in claim 15, further comprising, in response to a cursor over the overlay, indicating the depth of the at least one structure located below the surface of the anatomical region by an alphanumeric label indicating the depth.

* * * * *